US012606758B2

(12) United States Patent (10) Patent No.: US 12,606,758 B2

Obrist (45) Date of Patent: Apr. 21, 2026

(54) METHOD OF PRODUCING LIQUID FUEL BLEND USING A CARBON REDUCING PROCESS

(71) Applicant: OBRIST TECHNOLOGIES GMBH, Lustenau (AT)

(72) Inventor: Frank Obrist, Bregenz (AT)

(73) Assignee: OBRIST TECHNOLOGIES GMBH, Lustenau (AT)

( * ) Notice: Subject to any disclaimer, the term of this patent is extended or adjusted under 35 U.S.C. 154(b) by 0 days.

(21) Appl. No.: 18/845,731

(22) PCT Filed: Mar. 9, 2023

(86) PCT No.: PCT/EP2023/056009

§ 371 (c)(1),
(2) Date: Sep. 10, 2024

(87) PCT Pub. No.: WO2023/170204

PCT Pub. Date: Sep. 14, 2023

(65) Prior Publication Data

US 2025/0215338 A1 Jul. 3, 2025

(30) Foreign Application Priority Data

Mar. 11, 2022 (DE) .......................... 102022105802.6

(51) Int. Cl.

| | |
|---|---|
| *C10L 1/182* | (2006.01) |
| *C07C 29/152* | (2006.01) |
| *C10L 1/02* | (2006.01) |
| *C25B 1/04* | (2021.01) |

(52) U.S. Cl.
CPC .......... *C10L 1/1824* (2013.01); *C07C 29/152* (2013.01); *C10L 1/023* (2013.01); *C25B 1/04* (2013.01); *C10L 2200/0423* (2013.01)

(58) Field of Classification Search
CPC ................... C10L 1/023; C10L 1/1824; C10L 2200/0423; C07C 29/152; C07C 31/04; C25B 1/04

See application file for complete search history.

(56) References Cited

U.S. PATENT DOCUMENTS

| | | | |
|---|---|---|---|
| 6,571,747 B1 * | 6/2003 | Gerstweiler | ........ C07C 29/1518 123/3 |
| 2009/0172997 A1 | 7/2009 | Olah | |
| 2012/0198884 A1 * | 8/2012 | Golben | ..................... C10L 1/04 422/600 |

OTHER PUBLICATIONS

International Search Report and Written Opinion received for PCT Application No. PCT/EP2023/056009 on May 22, 2023, 9 pgs.

(Continued)

*Primary Examiner* — Latosha Hines

(74) *Attorney, Agent, or Firm* — Merchant & Gould P.C.

(57) ABSTRACT

The invention relates to a method of producing a liquid fuel blend for use in conventional combustion engines, wherein a methanol component is produced in an atmospheric carbon dioxide reducing process that is autonomously powered, in particular exclusively, by at least one renewable energy source, wherein the methanol component is mixed with an alcohol component and a fossil fuel component and the methanol component is produced by a process that actively removes carbon dioxide from the atmosphere.

6 Claims, 2 Drawing Sheets

(56) References Cited

OTHER PUBLICATIONS

Pearson, Richard, et al., "Energy Storage via Carbon-Neutral Fuels Made from CO2, Water, and Renewable Energy", Porceedings of the IEEE, Feb. 1, 2012, 21 pgs.

Nuria Sanchez-Bastardo, et al., "Methane Pyrolysis for CO2-Free H2 Production: A Green Process to Overcome Renewable Energies Unsteadiness", Chemie Ingenieur Technik, Wiley VCH. Verlag, Weinheim, Aug. 25, 2020, 14 pgs.

* cited by examiner

METHOD OF PRODUCING LIQUID FUEL BLEND USING A CARBON REDUCING PROCESS

CROSS-REFERENCE TO RELATED APPLICATIONS

The present application is a National Stage Application of PCT International Application No.: PCT/EP2023/056009 filed on Mar. 9, 2023, which claims priority to German Patent Application 10 2022 105 802.6, filed with the German Patent Office on Mar. 11, 2022. The disclosures of each application are incorporated herein by reference in their entirety.

TECHNICAL FIELD

The invention relates to a method of producing a liquid fuel blend using a carbon reducing process. The invention further relates to a use of methanol produced by the carbon reducing process as a portion of a liquid fuel blend.

TECHNICAL BACKGROUND

Since the beginning of the industrial revolution in 1800, the atmospheric $CO_2$ concentration has increased from a previously stable 280 ppmv (parts per million by volume) to 410 ppmv in the year 2020. It is predicted this increase will continue, or respectively intensify, if no carbon mitigation techniques are adopted to curb emissions.

The ratified Paris Agreement cites its main objective as keeping the increase in the average global temperature below 2° C. above pre-industrial levels, which requires a reduction in $CO_2$ emissions to zero by 2050. Proposals for limiting these emissions include the use of biofuels, solar power and wind turbines. However, reducing the past $CO_2$ emissions, thus limiting the increase in the atmosphere's $CO_2$ content, is not enough over the long term in order to rectify the imbalance of oxygen and $CO_2$ in the atmosphere resulting from an overproduction of $CO_2$ to date.

Vehicle infrastructure today is mainly based on liquid fuels, in particular fossil fuels. In order to reduce $CO_2$ emissions produced by burning fossil fuel, fuel blends containing $CO_2$ neutral components have been developed. The resulting fuel blend should be usable in existing combustion engines, in particular in existing cars. The most commonly used liquid fuel blend in Europe is called E10 gasoline, a liquid fuel blend containing about 90% (fossil) gasoline and 10% ethanol. A more recent development is a liquid fuel blend containing about 80% (fossil) gasoline, about 5% ethanol and about 15% methanol. This liquid fuel blend is called A20 and shows a significant reduction of $CO_2$ emissions by about 8% (well to wheel) compared to pure gasoline. Nevertheless, the use of A20 still leads to a significant emission of $CO_2$ and there is a need for further reduction of $CO_2$ emissions, at least until it is possible to actively reduce the atmospheric $CO_2$ content.

The invention therefore seeks to provide a method of producing a liquid fuel blend for use in conventional combustion engines, which liquid fuel blend has a reduced carbon fingerprint.

The invention provides a solution by the subject matter of claim 1.

Specifically, the invention provides for a method of producing a liquid fuel blend for use in conventional combustion engines, wherein a methanol component is produced in an atmospheric carbon dioxide reducing process that is autonomously powered, in particular exclusively, by at least one renewable energy source, the carbon dioxide reducing process including the following steps:

producing oxygen in an electrolysis unit which intakes a water volume $M_{H2O}$, in particular from the sea, via at least one water supply line and breaks down the intake water volume $M_{H2O}$ into an oxygen quantity $M_{O2}$ and a hydrogen quantity;

conveying a first portion of the hydrogen quantity from the electrolysis unit to a carbonization unit and a second portion of the hydrogen quantity to a methanol synthesis unit;

scrubbing of ambient air UL in at least one carbon dioxide sorption unit 12, the carbon dioxide sorption unit receiving the ambient air UL via at least one air inlet and extracting a carbon dioxide quantity from the ambient air UL in at least one downstream sorber device;

conveying a first portion of the carbon dioxide quantity to the carbonization unit and a second portion of the carbon dioxide quantity to the methanol synthesis unit;

producing carbon in the carbonization unit by methane synthesis and methane splitting, the methane splitting being effected by Kvaerner processing and/or monolith processing, and transporting the carbon to a long-term carbon storage, in particular an area of the seafloor, combining the second portion of the hydrogen quantity and the second portion of the carbon dioxide quantity in the methanol synthesis unit to produce the methanol component, and wherein the method further includes the step of mixing the methanol with an alcohol component and a fossil fuel component.

In a preferred embodiment of the inventive method, the methanol is mixed with an alcohol component and a fossil fuel component in a ratio such that the liquid fuel blend contains no more than 80% by volume of the fossil fuel component, at least 5% by volume of the alcohol component, and at least 15% by volume of the methanol component.

In a further preferred embodiment, the methanol component is mixed with the alcohol component and the fossil fuel component in a ratio such that the liquid fuel blend contains between 50%, in particular 65%, and 80% by volume of the fossil fuel component, between 5% to 20% by volume of the alcohol component, and between 10% to 30%, in particular 15%, by volume of the methanol component.

The liquid fuel blend resulting from the inventive process contains preferably a methanol component that has at least a zero, in particular a negative, carbon footprint, since the process for producing the methanol component actively reduces the $CO_2$ content in the atmosphere and thus reverses a part of the $CO_2$ emitting industrial processes of the last century. This methanol component is called C-sink methanol hereinafter. As a result, the well to wheel emissions of $CO_2$ are further reduced by a significant number. In particular, it is expected that the $CO_2$ emissions of the C-sink methanol are at least about 30%, in particular 38%, lower that the $CO_2$ emissions of pure gasoline. The inventive method therefore provides for significant reduction of ongoing $CO_2$ emissions and could thus be used to provide a liquid fuel blend for existing combustion engines until the existing combustion engines are replaced by engines which can be driven by more sustainable fuels or energy sources. Such future engines could be combustion engines that are designed to use C-sink methanol only.

In a preferred embodiment, the renewable energy source is at least one photovoltaic unit for converting solar energy into power. The photovoltaic unit may be located in a region having an global horizontal solar irradiation per year of at least 1.500 kWh/m$^2$, in particular 2000 kWh/m$^2$. The issue of increasing $CO_2$ emissions is global and thus a global endeavor is needed to solve this problem and to save the global climate. Therefore, it is desired to run the inventive method efficiently at large scale. Using photovoltaics as an renewable energy source has the advantage that the regions which have a high global horizontal solar irradiation also often have access to the sea. Thus, plants for applying the inventive method can be operated in a very efficient way, since all necessary source components, solar energy, $CO_2$ and water, are available at short distance. Moreover, generating energy by a photovoltaic unit is very cost efficient. In comparison with other technologies for renewable energy production, producing energy with photovoltaics is three to ten times less expensive. This applies in particular when the method is executed in a plant located in a region having long hours of sunshine or a high global horizontal solar irradiation, e.g. in Saudi Arabia.

The method allows for producing pure oxygen and absorbing carbon dioxide in a continuous process, thus actively removing $CO_2$ from the atmosphere. Burning the fuel blend having C-sink methanol therefore leads to less $CO_2$ emissions compared to any other known liquid fuel blend that is suitable to be used in existing combustion engines. Feeding the carbon produced in the carbonization unit to a carbon store is preferred to actively reduce the $CO_2$ content in the atmosphere. The carbon store can in particular be a sea or a seafloor respectively. In other words, the carbon, in particular in the form of graphite, can be permanently stored on the seafloor.

Extracting the carbon component from the atmosphere may be effected by a two-stage process, namely methane synthesis followed by a methane splitting. For the methane splitting, a Kvaerner process may be used. Alternatively, the methane splitting may comprise a methane pyrolysis process, called monolith process. (Waste) Heat from the carbonization process, in particular the methane splitting, may be conveyed to the carbon dioxide sorption unit and used there as energy for the carbon sorption. Additionally, (waste) heat from the methanol synthesis may be conveyed to the carbon dioxide sorption unit and used there as energy for the carbon sorption.

In a preferred embodiment of the method according to the invention, the oxygen quantity and the purified ambient air are released into the outside atmosphere and the hydrogen quantity and the volume of carbon dioxide are converted to water, carbon and heat in the carbonization unit. The carbonization unit may comprise a Bosch reactor or a Kvaerner processing unit or a $CO_2$ plasma torch unit. This enables a reduction in the carbon dioxide content in the atmospheric air and thus the equalizing of an existing imbalance in the volume of the air's constituent parts.

The heat ensuing from carbonization in the carbonization unit can be conveyed to the carbon dioxide sorption unit and used there as energy for the carbon sorption. Additionally or alternatively, the heat ensuing from the methanol synthesis unit can be conveyed to the carbon dioxide sorption unit and used there as energy for the carbon sorption. The efficiency of the overall method is thus further increased and the primary energy need of the plant or method respectively reduced.

It is preferred that the fossil fuel component is gasoline. Refining crude oil to receive gasoline may be executed using power generated by, in particular exclusively, renewable energy sources. The alcohol component may generally different from methanol and may be preferably ethanol, in particular synthetic ethanol produced by using, in particular exclusively, power of at least one renewable energy source.

The overall aim of the invention is to decrease the fossil fuel component by increasing the content of the methanol and/or ethanol component in the liquid fuel blend. This process may take several years, but could be a way to meet current energy needs while reducing $CO_2$ emissions until new engines are available on a larger scale that can run on a liquid fuel blend containing more methanol. It may be considered, e.g., to provide a liquid fuel blend containing 80% by volume gasoline, 5% by volume ethanol and 15% by volume C-sink methanol until the year 2030, then increasing the portion of methanol and providing a liquid fuel blend containing 50% by volume of gasoline, 15% by volume of ethanol and 15% by volume of C-sink methanol.

The latter liquid fuel blend could be provided until the year 2040 for operating existing combustion engines. At the same time, in particular from 2030 onwards, a new fuel blend may be used for future engines that are designed to be operated by this new fuel blend. The new fuel blend may include no fossil fuel component but containing methanol only, wherein a portion of the methanol is C-sink methanol. In particular, the new fuel blend, called aFuel, may in the first years of its introduction, comprise 90% by volume of methanol produced by using exclusively renewable energy sources, so called eMethanol, and 10% by volume of C-Sink methanol. This aFuel may have −110% of $CO_2$ emissions by calculation.

The method of producing this aFuel would thus decrease the content of $CO_2$ in the atmosphere actively. After a period of time, e.g. from 2040 onwards, the composition of the aFuel could be changed to 70% by volume of eMethanol and 30% by volume of C-sink methanol, thus having −130% of $CO_2$ emissions by calculation. From 2050 onwards, the aFuel may contain 50% by volume of eMethanol and 50% by volume of C-sink methanol, thus leading to calculated $CO_2$ emissions of −150% by volume. It is clear from the above numbers that burning aFuel actively reduces the $CO_2$ content in the atmosphere due to the specific process of producing the C-sink methanol.

BRIEF DESCRIPTION OF THE DRAWINGS

The invention will be hereinafter described in greater detail on the basis of further details referencing the accompanying drawings. These drawings show.

DETAILED DESCRIPTION OF THE INVENTION

Figure 1:
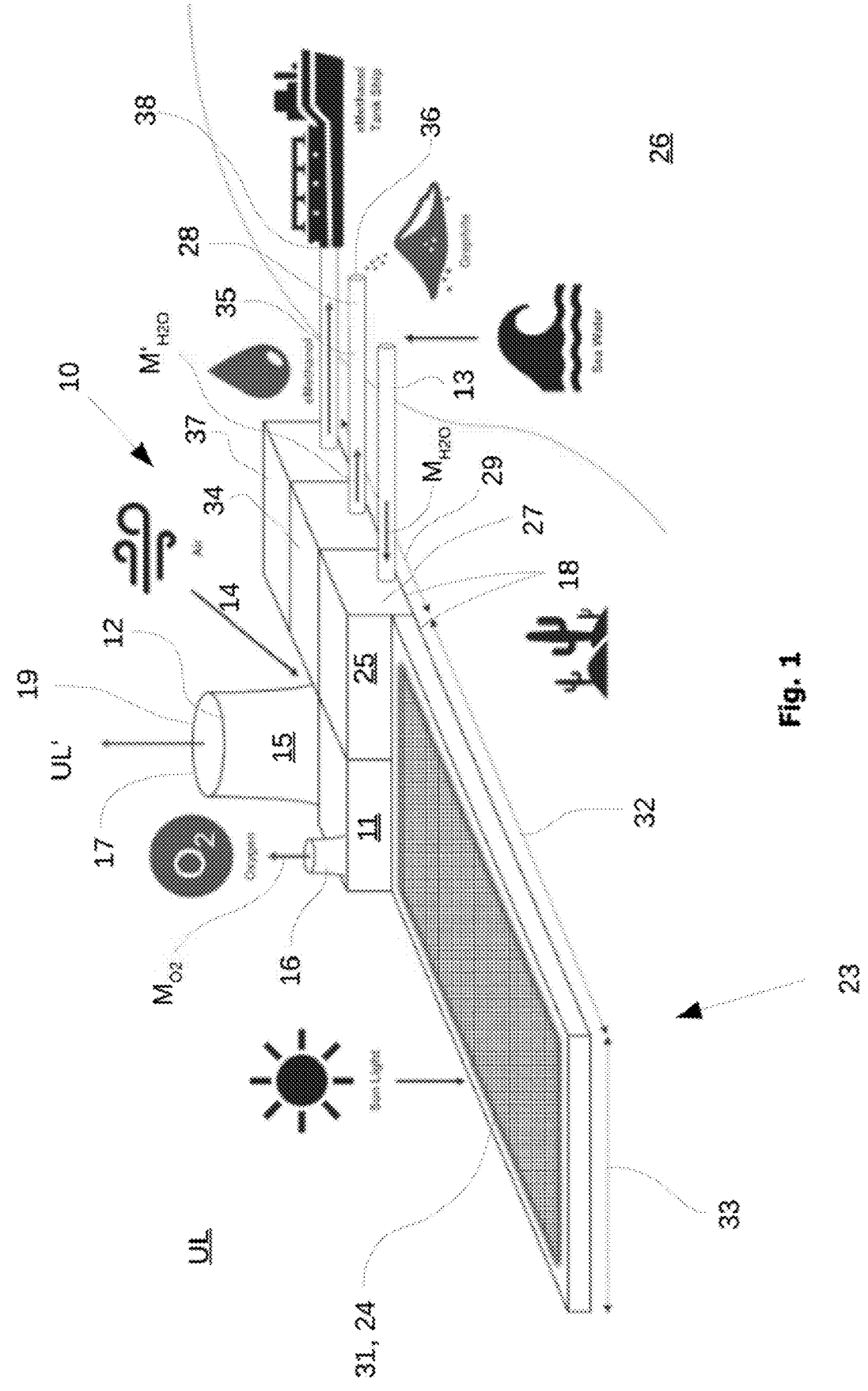
FIG. 1 a perspective view of an plant for the reduction of the carbon dioxide content in atmospheric air and for the production of C-sink methanol according to a preferred embodiment of the inventive method.

The inventive method is preferably performed by a plant 10 located in an area of high global horizontal solar irradiation and close to the sea, e.g. in Saudi Arabia. The plant 10 according to FIG. 1 is a large-scale power plant. The plant 10 exhibits at least one mounting area 18 which is attached to a foundation of a building and/or structure. It is generally possible for the electrolysis unit 11 and/or the carbon dioxide sorption unit 12 to be arranged in a communal building or in separate buildings.

The plant 10 may comprise an electrolysis unit 11 for the production of oxygen and a carbon dioxide sorption unit 12 for the scrubbing of ambient air UL of the outside atmosphere surrounding the plant 10. The plant 10 may further comprise a power generation unit 31 for the autonomous power supply of the plant 10, which will subsequently be discussed in greater detail.

The electrolysis unit 11 is designed to break down a water volume $M_{H2O}$ into a oxygen quantity $M_{O2}$ and a hydrogen quantity by electrolysis. The electrolysis unit 11 thus forms a hydro-electrolysis unit. The electrolysis unit 11 is connected to a water supply line 13 for intaking the water volume $M_{H2O}$. As can be seen in FIG. 1, a pump unit 25 is arranged between the electrolysis unit 11 and the water supply line 13. The pump unit 25 comprises at least one pump for conveying water from a water reservoir 26. The water reservoir 26 can be a sea containing seawater.

In order to prepare the seawater for the electrolysis process via the electrolysis unit 11, the plant 10 comprises a seawater desalination unit 27. The seawater desalination unit 27 is adapted to remove a certain amount of salt from the extracted seawater $M_{H2O}$ so that the seawater has a reduced salt content after the desalinization process in the seawater desalination unit 27. The desalinated volume of seawater $M_{H2O}$ corresponds to the water volume $M_{H2O}$ broken down by the electrolysis unit 11 into a oxygen quantity $M_{O2}$ and a hydrogen quantity. The electrolysis unit 11 is connected to the seawater desalination unit 27 by at least one pipeline. To output the oxygen quantity $M_{O2}$ produced, the electrolysis unit 11 has an oxygen outlet 16 which discharges into the outside atmosphere. It is possible for the electrolysis unit 11 to exhibit one or more oxygen outlets 16 for the output of the oxygen quantity $M_{O2}$ produced.

The plant 10 further comprises at least one (not depicted) hydrogen transport mechanism adapted to provide a first portion of the hydrogen quantity separated from the water volume $M_{H2O}$ to a carbonization unit 34 for further processing. A second portion of the hydrogen quantity may be fed to a methanol synthesis unit 37.

As per FIG. 1, the carbon dioxide sorption unit 12 has an air inlet 14 for the supply of the ambient air UL and a downstream sorber device 15. It is possible for the carbon dioxide sorption unit 12 to have one or more air inlets 14. The sorber device 15 is connected to the air inlet 14. The sorber device 15 is adapted to extract a volume of carbon dioxide from the ambient air UL. The carbon dioxide sorption unit 12 further exhibits an air outlet 17. The air outlet 17 serves to release ambient air UL' which has been scrubbed of carbon dioxide. The air outlet 17 can be oriented vertically upwards and/or be part of a flue 19.

Specifically, the sorber device 15 is arranged between the air inlet 14 and the air outlet 17. In operation, the ambient air UL flows through the air inlet 14 to the sorber device 15 which removes, in particular filters, a specific quantity of carbon dioxide from the air UL, whereby the purified ambient air UL' flows through the air outlet 17 into the outside atmosphere following the sorber device 15.

The plant 10 moreover comprises a carbon dioxide transport mechanism which is designed to provide the carbon dioxide volume separated from the ambient air UL to the carbonization unit 34 of the plant 10 for further processing. Preferably, the carbonization unit 34 is thus supplied the first portion of the hydrogen quantity and the first portion of the carbon dioxide quantity so that the extracted carbon dioxide quantity is processed with the separated hydrogen quantity into further intermediate and/or end products. Specifically, at the first portion of the carbon dioxide quantity and the second portion of the hydrogen quantity can be converted to water, carbon (graphite) and heat by methanisation realized in the carbonization unit (34).

As shown in FIG. 1, the plant 10 comprises an areal plant region 23. The areal plant region 23 directly connects to the electrolysis unit 11. A power generation unit 31, which is a photovoltaic unit 24, is arranged on the areal plant region 23. The photovoltaic unit 24 is connected to the respective units of the plant 10 for power supply. The photovoltaic unit 24 is adapted such that the entire plant 10 can be operated in energy-autonomous manner. That means that the electrical power for operating the entire plant 10 is provided exclusively by solar energy via the photovoltaic unit 24. In other words, no fossil energy sources are used in operating the plant 10. The power supply unit 31 preferentially comprises a (not depicted) energy store adapted to supply power to the plant 10 during nighttime operation.

The above-described seawater desalination unit 27 is connected to a water return line 28 through which a volume of seawater of increased salt content to be recirculated $M'_{H2O}$ is returned to the sea. Specifically, a certain salt content is extracted from the withdrawn volume of seawater and then returned to the sea along with part of the withdrawn volume of seawater as the recirculated water volume $M'_{H2O}$. This provides a water cycle which is not harmful to nature.

The plant 10 further includes a methanol synthesis unit 37. The methanol synthesis unit 37 is connected to the electrolysis unit 11 by a hydrogen transport mechanism and to the carbon dioxide sorption unit 12 by a carbon transport mechanism. The methanol synthesis unit 37 synthesizes methanol from the supplied hydrogen and carbon which can be removed from the plant 10 via a methanol outlet 38. The methanol can be distributed to decentralized methanol distribution sites world-wide, in particular by means of a fuel distribution system, which can include ships, in particular tankers, tanker trains and/or tanker trucks. The methanol distribution sites can be filling stations providing methanol for refueling motor vehicles, aircraft, ships or locomotives.

The appropriate control of the method in the plant 10 enables regulating the amount of the carbon sorbed in the carbon dioxide sorption unit which is used for the production of the liquid fuel blend or for the production of graphite for storage in a carbon store. Initially, a ratio of 20% graphite and 80% methanol is likely appropriate, whereby the percentage of methanol will be gradually reduced and the percentage of graphite increased in the process when the need for methanol production shrinks, particularly upon the building of further plants 10.

The following will describe the method for operating the plant 10 according to FIG. 1 and thus for producing C-sink methanol in greater detail.

In a first method step, a water volume $M_{H2O}$ is taken up through the water supply line 13 via the electrolysis unit 11 for the production of oxygen. An electrolysis process subsequently breaks down the volume of intake water $M_{H2O}$ into an oxygen quantity $M_{O2}$ and a hydrogen quantity. The hydrogen quantity is made available to a carbonization unit 34 for further processing by at least one hydrogen transport mechanism, wherein the carbonization unit 34 in the present exemplary embodiment effects a methanisation process that comprises methan synthesis and methane splitting.

In a second method step, ambient air UL of an outside atmosphere surrounding the plant 10 is scrubbed by the carbon dioxide sorption unit 12. The ambient air UL is fed, in particular drawn into the flow channels 21 through a plurality of air intakes 14 and supplied to the downstream sorber devices 15. The sorber devices 15 subsequently extract a carbon dioxide quantity from the supplied ambient air UL. A first portion of the carbon dioxide quantity is fed to the carbonization unit 34 for methanisation via the carbon dioxide transport mechanism. The oxygen quantity $M_{O2}$ obtained following the decomposition process and the scrubbed ambient air UL' after the volume of carbon dioxide has been extracted are thereafter released into the outside atmosphere. The oxygen content in the air is thereby increased and the $CO_2$ content in the air reduced.

The first portion of the hydrogen quantity together with the first portion of the carbon dioxide quantity is furthermore converted into water, carbon, respectively graphite and heat, by means of the methanisation process ng.

In the method, seawater is desalinated and the desalinated seawater then split into the hydrogen quantity and the oxygen quantity by means of electrolysis. The oxygen $O_2$ is released into the ambient air, the atmosphere in particular, such that the oxygen content in the environment of the plant is increased. Parallel to that, carbon dioxide $CO_2$ is collected from the ambient air UL, the atmosphere in particular, by carbon dioxide sorption. As with the electrolytically generated hydrogen, or the hydrogen quantity respectively, the first portion of the carbon dioxide quantity taken from the ambient air UL is conducted to the carbonization unit 34.

The carbon or respectively graphite can subsequently be fed to a carbon store via the carbon transport mechanism 35. The carbon store can for example be the water reservoir 26 or respectively the sea. Since the graphite produced in the methanisation process exhibits barely any to no impurities and is solidified like rock, there are no concerns related to dumping the graphite in the sea.

Besides the carbon reducing process as mentioned above, a second portion of the hydrogen quantity and a second portion of the carbon dioxide quantity are fed to the methanol synthesis unit 37 and combined therein to produce the methanol component, i.e. C-sink methanol. Waste products, like hydrogen and/or oxygen, from the methanisation process may be used for methanol synthesis.

The energy needed for the electrolysis, the carbon dioxide sorption and the methanisation originates from renewable energy sources, specifically the photovoltaic unit 24, such that there is thereby no additional production of carbon dioxide.

With the method described herein, it is therefore possible to efficiently remove carbon dioxide from the earth's atmosphere and separate it into in its graphite and oxygen components while simultaneously produce a methanol component that can be used to mix a liquid fuel blend having less impact on climate change than any other known fuel blend including fossil fuel. The oxygen can be returned to the atmosphere and the graphite permanently stored in a carbon store, for example the sea.

The inventive method produces $CO_2$-removing methanol (C-sink methanol). During the production of C-sink methanol, $CO_2$ is removed from atmospheric air and the excess carbon is stored in a carbon store. The method thus efficiently achieves an improvement in atmospheric air quality.

The liquid fuel blend produced by the inventive thus has significant lower $CO_2$ well-to-wheel emissions than pure gasoline.

Figure 2:
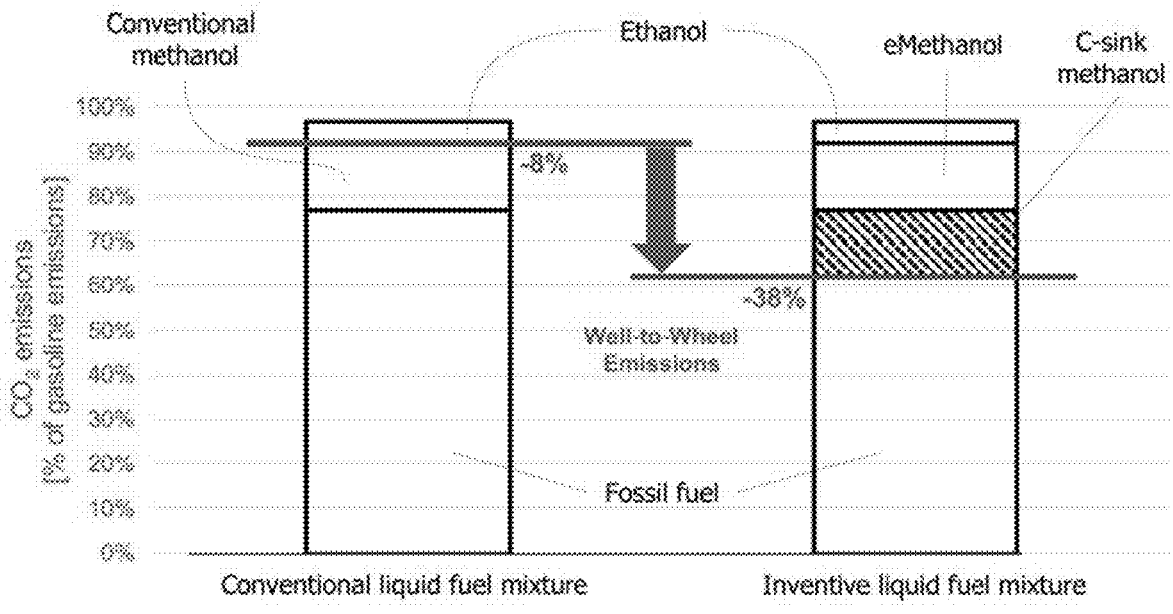
FIG. 2 a chart comparing the $CO_2$ reducing effect of a conventionally produced liquid fuel blend containing gasoline, methanol and ethanol with a liquid fuel blend as produced by the present invention.

As shown in FIG. 2, the well-to-wheel emissions of a conventional liquid fuel blend containing methanol are reduced by 8% compared to pure gasoline already. However, with the inventive method of production, the well-to-wheel emissions of $CO_2$ can be reduced by 38% compared to pure gasoline. If one extrapolates this to existing large fleets of vehicles having conventional combustion engines, e.g. for postal services or freight transport, the $CO_2$ reduction is significant and will have an impact on slowing down climate change.

Figure 3:
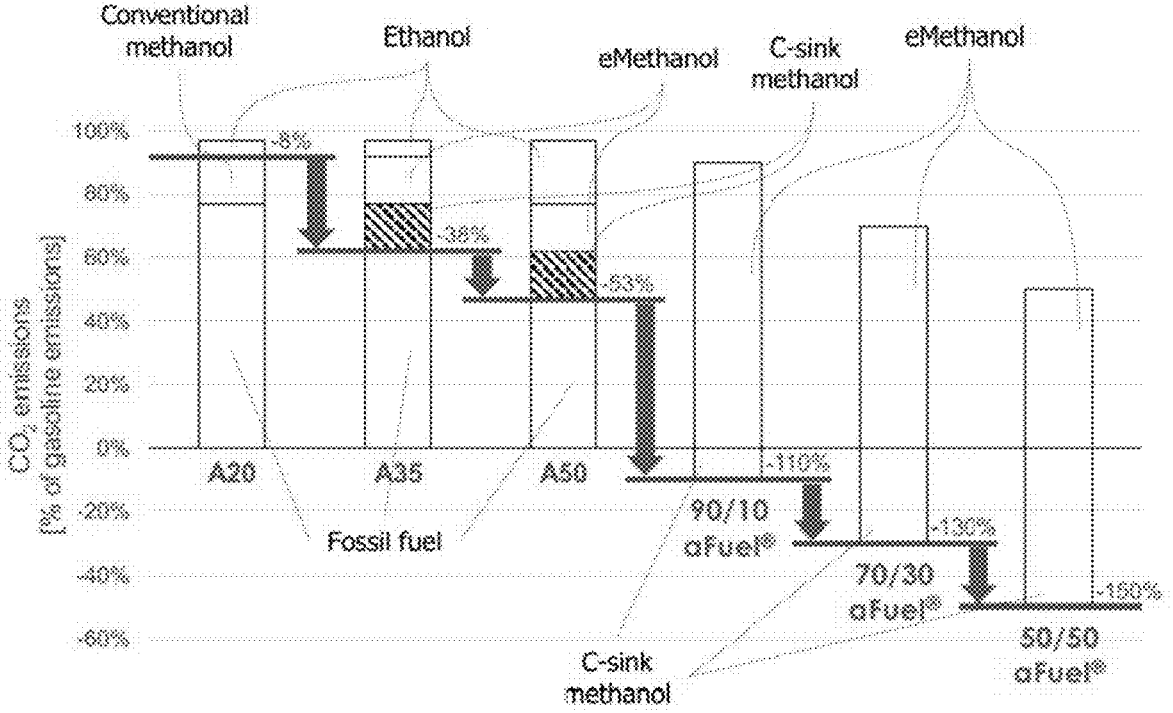
FIG. 3 a chart showing the transition to a $CO_2$ decreasing liquid fuel solution by using a liquid fuel blend as produced by the present invention.

Nevertheless, additional efforts should be taken in order to further move towards a more sustainable world. FIG. 3 shows a possible timetable for introducing different backwards compatible liquid fuel blends and simultaneously introducing a new fuel for future combustion engines.

As shown in the chart of FIG. 3, the conventional liquid fuel blend containing 80% by volume of gasoline, 5% by volume of ethanol and 15% by volume of conventionally produced methanol could be used until the new liquid fuel blend, produced by the inventive method, is ready for series production. The new liquid fuel blend including C-sink methanol is adapted to be used in the existing vehicle fleet and may then be further adopted to the change of the composition of the existing vehicle fleet. The change of the composition of the existing vehicle fleet will result from older vehicles being removed from the fleet. More recent vehicles would be able to tolerate a liquid fuel blend containing a larger content of methanol. Thus, from 2040 onwards, a liquid fuel blend containing more than 15% by volume of C-sink methanol could be used.

Simultaneously, new vehicles with combustion engines will be developed and designed to accommodate to a new fuel containing methanol only. At least a portion of the methanol could then be C-sink methanol. The remainder of the methanol could preferably be eMethanol produced by using power of renewable energy sources exclusively. As clearly derivable from FIG. 3, the introduction of this new fuel (aFuel) will then start a new era of actively reducing the $CO_2$ content in the atmospheric air.

LIST OF REFERENCE NUMERALS 10 plant
11 electrolysis unit
12 carbon dioxide sorption unit
13 water supply line
14 air inlet
15 sorber device
16 oxygen outlet
17 air outlet
18 mounting area
19 flue
23 areal plant region
24 photovoltaic unit
25 pump
26 water reservoir
27 seawater desalination unit
28 water return line
29 partial longitudinal extension
31 power generation unit
32 longitudinal extension
33 transverse width
34 carbonization unit
35 carbon transport mechanism

36 carbon outlet
37 methanol synthesis unit
38 methanol outlet
UL ambient air
UL' scrubbed ambient air
$M_{H2O}$ withdrawn water volume
$M'_{H2O}$ recirculated water volume
$M_{O2}$ partial oxygen quantity
The invention claimed is:

1. A method of producing a liquid fuel blend for use in conventional combustion engines, the liquid fuel blend comprising methanol, an alcohol, and a fossil fuel, wherein the methanol is produced in an atmospheric carbon dioxide reducing process that is autonomously powered by at least one renewable energy source, the carbon dioxide reducing process including the following steps:

producing oxygen in an electrolysis unit which intakes water via at least one water supply line and breaks down the water into an oxygen quantity and a hydrogen quantity;

conveying a first portion of the hydrogen quantity from the electrolysis unit to a carbonization unit and a second portion of the hydrogen quantity to a methanol synthesis unit;

scrubbing of ambient air in at least one carbon dioxide sorption unit, the carbon dioxide sorption unit receiving the ambient air via at least one air inlet and extracting a carbon dioxide quantity from the ambient air in at least one downstream sorber device;

conveying a first portion of the carbon dioxide quantity to the carbonization unit and a second portion of the carbon dioxide quantity to the methanol synthesis unit;

producing carbon in the carbonization unit by methane synthesis and methane splitting, wherein the methane splitting is by Kvaerner processing and/or methane pyrolysis, and transporting the carbon to a long-term carbon storage, and combining the second portion of the hydrogen quantity and the second portion of the carbon dioxide quantity in the methanol synthesis unit to produce the methanol, wherein the methanol is mixed with the alcohol and the fossil fuel in a ratio such that the liquid fuel blend contains 50% to 80% by volume of the fossil fuel, 5% to 20% by volume of the alcohol, and 10% to 30% by volume of the methanol, and wherein the at least one renewable energy source is at least one photovoltaic unit for converting solar energy into power, the photovoltaic unit being located in a region having a global horizontal solar irradiation per year of at least 1.500 kWh/m².

2. The method according to claim 1, wherein, heat from the carbonization unit is conveyed to the carbon dioxide sorption unit and used there as energy for the carbon sorption.

3. The method according to claim 1, wherein, heat from the methanol synthesis unit is conveyed to the carbon dioxide sorption unit and used there as energy for the carbon sorption.

4. The method according to claim 1, wherein, the fossil fuel is gasoline.

5. The method according to claim 1, wherein, the alcohol is ethanol that is produced by using, power of at least one renewable energy source.

6. The method according to claim 1, wherein, at least a portion of hydrogen and/or oxygen produced by the carbonization unit is conveyed to the methanol synthesis unit and used to produce the methanol.

\*    \*    \*    \*    \*